United States Patent [19]

Lawson et al.

[11] Patent Number: 4,975,648

[45] Date of Patent: Dec. 4, 1990

[54] DISCHARGE IONIZATION DETECTOR

[75] Inventors: Alexander E. Lawson, Mendham Township; Morris County, N.J.; Robert J. Mathieu, Solebury, Pa.

[73] Assignee: Gow-Mac Instrument Co., Bridgewater, N.J.

[21] Appl. No.: 383,653

[22] Filed: Jul. 24, 1989

[51] Int. Cl.$^5$ ............................................. G01N 27/70
[52] U.S. Cl. ..................................... 324/464; 324/459; 315/111.11; 315/111.91
[58] Field of Search ....................... 324/459, 464, 468; 315/111.11, 111.91; 250/379, 385.1

[56] References Cited

U.S. PATENT DOCUMENTS

| | | | |
|---|---|---|---|
| 3,454,828 | 7/1969 | Yamane | 315/111.91 |
| 4,114,088 | 9/1978 | Laws | 324/464 |
| 4,789,783 | 12/1988 | Cook | 250/385.1 X |

*Primary Examiner*—Gerard R. Strecker
*Assistant Examiner*—Jack B. Harvey

*Attorney, Agent, or Firm*—Morris Fidelman; Franklin D. Wolffe

[57] ABSTRACT

A discharge ionization detector which comprises with a cylindrical housing wherein is formed a discharge chamber at one end, and wherein is formed an ionization chamber at the other end an aperture connecting the chambers, arc electrodes being located in the discharge chamber, and emitter/collector electrodes being located in the ionization chamber, the latter comprising flat parallel plates, the housing being provided with an inlet into the discharge chamber for delivering discharge gas to the discharge chamber which discharge gas leaves the discharge chamber through the aforementioned aperture, with an inlet into the ionization chamber for delivering sample gas to the ionization chamber, and with an outlet from the ionization chamber for carrying the mixed discharge gas and sample gas out of the ionization chamber. The discharge gas and sample gas mix then pass between the flat parallel emitter/collector plates before leaving the ionization chamber through the outlet. The ionization chamber should be less than about 500 microliters in volume.

8 Claims, 2 Drawing Sheets

Fig. 1
Fig. 2
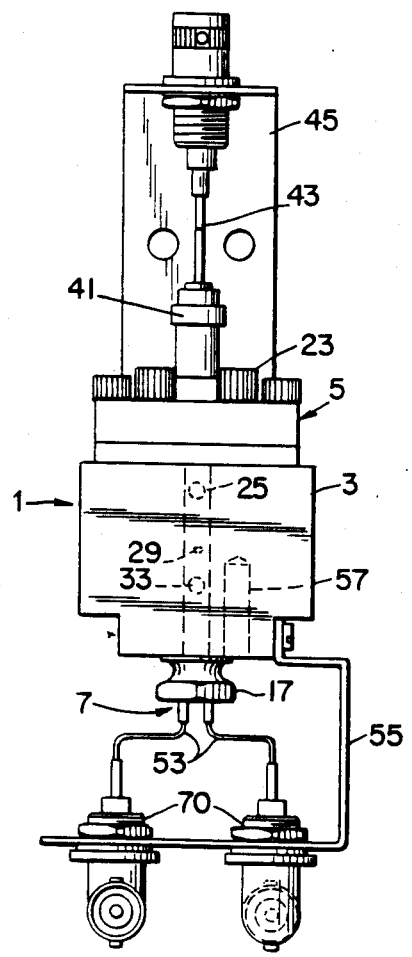
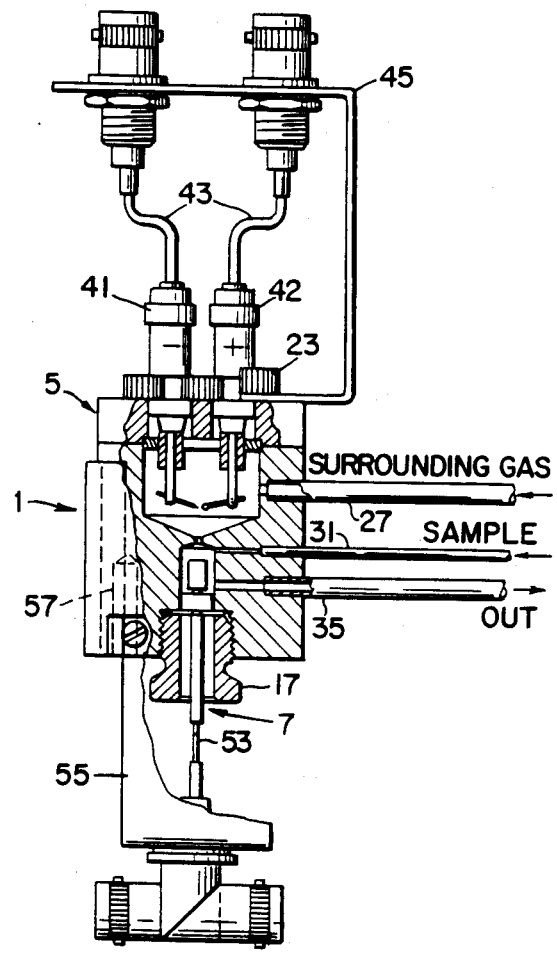

DISCHARGE IONIZATION DETECTOR

BACKGROUND OF THE INVENTION

This invention relates to an improved discharge ionization detector especially useful in detecting the gaseous components in a gas chromatography system.

Gas chromatograph systems separate an unknown substance into component parts so that the exact components of the unknown substance can be determined and identified Thus, once the unknown substance has been chromatographically separated into components, a detector of one sort or another is necessarY to detect the various components The type of detector to which this invention relates is the discharge ionization detector, or D.I.D.

In general, a D.I.D. operates by applying a high voltage across two discharge electrodes which are located in a gas filled discharge chamber. Typically, the gas may be helium, from which gas photons become discharged at a characteristic energy level. This "glow discharge" gas is directed toward an ionization chamber, into which sample gas (containing the unknown substance component(s)) from the gas chromatograph also is directed Inside the ionization chamber are two electrodes: one a negatively charged emitter electrode, the other a positively charged collector electrode. The glow discharge gas passing from the discharge chamber into the ionization chamber mixes with and interacts with the sample gas, causing electrons to be generated in the ionization chamber. These electrons are repelled by the emitter electrode and attracted by the collector electrode, causing a current to flow between these electrodes The magnitude of this current can be used to ascertain the composition of the unknown substance, all as is well known in the art. One such D.I.D. is shown by the U.S. Pat. No. 4,789,783 to Cook.

It has now been discovered by the inventors hereof that the exact geometry of the two chambers and of the emitter/collector electrodes in the D.I.D. are surprisingly important to the efficient operation of a D.I.D. In particular, the collector and emitter electrodes can be shaped and be positioned relative to the inlet for the sample gas and to the aperture (inlet) from the discharge chamber into the ionization chamber so that improved sensitivity for the D.I.D. results. The relative size of the chambers, a smaller ionization chamber in particular, is important for best sensitivity in the detector.

SUMMARY OF THE INVENTION

The D.I.D. of this invention contains a cylindrical housing containing a discharge chamber in one end thereof and an ionization chamber in the opposing end thereof; for convenience the discharge chamber end is called the first end and this first end is considered to be the top end. The discharge and ionization chambers have a common longitudinal axis; they are connected by an aperture.

An electric arc assembly is mounted on the housing preferably on the (first) end face adjacent the discharge chamber and the electrodes of the arc assembly are positioned inside the discharge chamber. An emitter/collector electrode assembly also is mounted on the housing preferably on the end face adjacent the ionization chamber and the emitter and the collector electrodes are positioned inside the ionization chamber. These electrodes comprise flat parallel plates. The high voltage source for the arc electrodes of the D.I.D. is, for example. 0–1000 Volts D C. across the electrodes. The voltage source for the emitter/collector electrode assembly supplies, for example, 160 Volts D.C.

The cylindrical housing is provided with an inlet in the side wall thereof leading into the discharge chamber. This inlet delivers the discharge gas (usually helium) to the discharge chamber. The housing also has a second inlet in the side wall, the second inlet leading into the ionization chamber and introducing sample gas thereto. Preferably, this second inlet is located so as to introduce the sample gas adjacent the aperture connecting the discharge and ionization chambers. Desirably this second inlet introduces the gas tangentially. Finally, an outlet is provided in the side wall of the housing for discharging gas from the ionization chamber. The aperture between the two chambers should be little more than a pin hole. A preferred ratio of the length to width for the aperture is less than 1.

The volume of the discharge chamber should be at least five times, preferably more than ten times, greater than the volume of the ionization chamber.

Preferably, both the discharge chamber and the ionization chamber like the housing are cylindrical. Preferably, the connecting wall between the chambers slopes toward the aperture. Such a construction may readily be machined out of bar stock and conveniently as well, the electrical connections which comprise the discharge arc assembly are mounted on and in one end face of the housing cylinder while the electrical connections which comprise the emitter/collector electrode assembly are mounted in and on the other end face of the housing cylinder.

The "parallel plate" arrangement for the emitter and collector electrodes is advantageous The glow discharge from the discharge chamber is directed between the plates. On the other hand, the sample gas sweeps in peripherally from the tangential inlet. The parallel plates cause the glow discharge and the sample gas to mix within the ionization chamber. In particular, the gas between the plates is a mixture. By making the ionization chamber small relative to the discharge chamber, a large glow discharge reservoir can be maintained. The small ionization chamber generates rapid response to changes in the sample.

All in all, the above features combine to create a remarkably efficient and sensitive DID.

BRIEF DESCRIPTION OF THE DRAWINGS

These and other features of the present invention will be evident from the following detailed description of the invention, the description being made in connection with the attached figures, in which:

FIG. 1 is a front view of the discharge ionization detector according to the present invention;

FIG. 2 is a side view of the D.I.D. of FIG. 1, showing part of the detector housing cut away;

DETAILED DESCRIPTION OF THE INVENTION

The discharge ionization detector (D.I.D.) according to the present invention includes a cylindrical housing 3, an electric arc assembly 5 at a first end face of the housing, and an emitter/collector electrode assembly 7 at the other or second end face of the housing.

Figure 3:
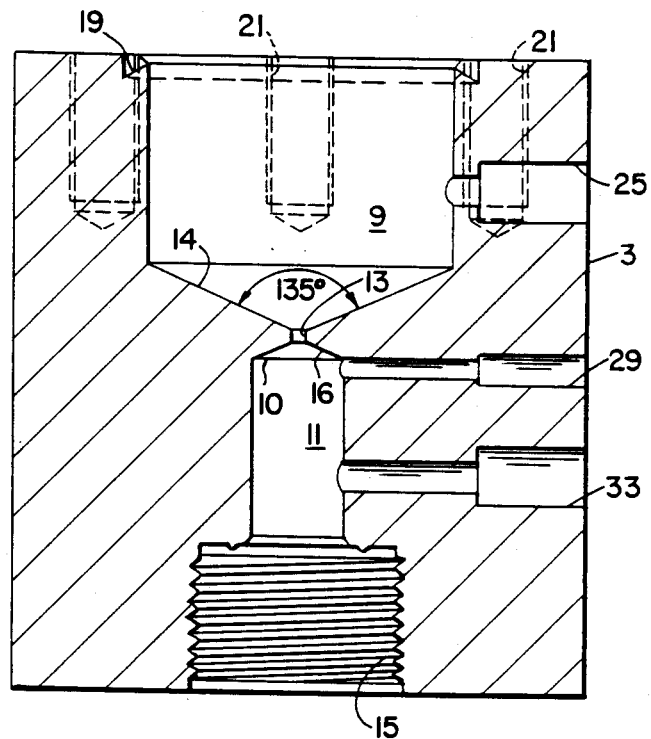
FIG. 3 is a vertical cross-section of the housing of the D.I.D. of FIG. 1.

The housing 3 itself is shown in greater detail in FIG. 3. As may be seen in that figure housing 3 may be a short length of bar stock drilled or tapped in the end faces to generate discharge chamber 9 and ionization chamber 11 separated by partition 10, and connected by the small pin hole size aperture 13 in wall 10. Preferably, the length of the aperture 13 is less than the diameter of the aperture. Like housing 3, the ionization chamber 11 and the discharge chamber 9 are cylindrical in shape, and preferably they share a common longitudinal axis. The wall surfaces 14, 16 on partition 10 are angled so as to slope toward the aperture 13. To repeat, the structure of housing 3 is most convenient from a manufacturing point of view.

The volume of discharge chamber 9 is much greater than the volume of ionization chamber 11; exemplary volumes for the particular DID illustrated in the drawing hereof are approximately 3.20 cm$^3$ for the discharge chamber, and 0.23 cm$^3$ for the ionization chamber.

As has already been indicated the ionization chamber should be a small cavity, i.e., less than about 500 microliters (0.5 cc) in volume. It has been determined that the D.I.D. is a concentration dependent detector, as opposed to a mass dependent type. The small volume ionization chamber provides excellent sensitivity.

Another benefit to a small cavity ionization chamber is that the D.I.D. will recover quickly from an overload, because of the relatively rapid turnover of gas in a cavity smaller than about 500 microliters.

At the bottom of the housing 3 is formed a tapped cavity 15 which communicates with the ionization chamber 11 and which is internally threaded for mounting the electrode engaging body 17 (see FIGS. 1 and 2) for the emitter/collector electrode assembly 7. At the top of housing 3 an annular rim 19 is cut into the end face of the housing. Annular rim 19 is adapted to seat a gasket (not shown well) between housing 3 and electric arc assembly 5. The gasket seats of discharge chamber 9. Several threaded bolt holes 21 in the end face of housing 3 are shown in phantom in FIG. 3. Bolts 23 (see FIGS. 1 and 2) connect electric arc assembly 5 with housing 3.

FIG. 3 shows the several inlet and outlet bore holes that extend through the side wall of housing 3 The top bore hole 25 is an inlet which communicates with discharge chamber 9. This inlet bore 25 is connected to pipe 27, which feeds discharge gas, e.g., helium, to discharge chamber 9. A second inlet bore hole 29 communicates to the ionization chamber 11, at the top thereof and is connected to a pipe 31 which carries the sample gas from a chromatograph column (not shown) to the D.I.D. Finally, an outlet bore hole 33 communicates with the ionization chamber near the bottom thereof, and is connected to outlet pipe 35 which carries the mixture of the sample gas and discharge gas away from the D.I.D. The three bore holes 25, 29 and 33 may be in line relative to the vertical axis of the housing or be offset, the latter being shown in FIG. 1. The inlet bore hole 25 extends radially of the discharge chamber 9. The inlet bore hole 29 and outlet 33 extend tangentially into ionization chamber 11 near the top and bottom of the ionization chamber 11 respectively. Since the flat electrode face plates 48, 50 of emitter/collector electrode assembly 7 so nearly fill the ionization chamber 11, both bore holes 29, 33 and aperture are adjacent plates 48, 50.

Figure 4:
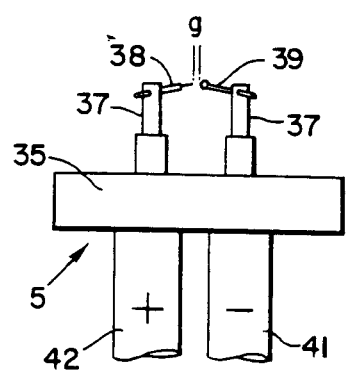
FIG. 4 is a side view of the electric arc assembly of the D.I.D. of FIG. 1.

The electric arc assembly 5 is shown in greater detail in FIG. 4. As may be seen in that figure, a sealing flange 35 supports two cylindrical pins 37. Attached to the pins are electrodes 38 and 39. The electrode 38 is preferably made of tungsten and is sharpened to a point. Electrode 39 is preferably made of platinum and has a small ball at the end thereof. Desirably, the electrodes 38 and 39 are angled to terminate at the top of posts 37, or above posts 37. They are mounted so that a small gap g exists between the point of electrode 38 and the ball of electrode 39. The gap g which, for example, may be about 0.6 mm is two or three times the diameter of wires 38, 39. The pins 37 are connected to the insulating plugs 41 and 42, which are in turn connected to wires 43 (see FIG. 2), which lead to cable couplings 44 and in turn lead to a source of high voltage (not shown).

A bracket 45 connected to the housing 3 through one or more of the bolts 23, and connected to cable couplings 44 support the electrical connections of the electric arc assembly 5 and maintain the wires 43 in proper spaced apart relation. If desired, the bracket 45 can be used for a connection of the detector 1 to a gas chromatograph apparatus.

Figure 5:
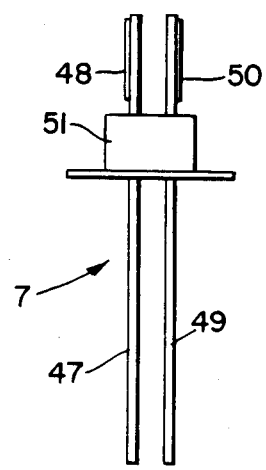
FIG. 5 is a side view of the emitter/collector electrode assembly of the D.I.D. of FIG. 1.

The emitter/collector electrode assembly 7 is shown in detail on FIG. 5. As may be seen in that figure, an insulated emitter electrode lead 47 and an insulated collector electrode lead 49, both of which are typical (cylindrical) electrical wire, connect through an insulator base 51 which serves a spacing function to the bare wires of electrodes 48 and 50. A generally flat, rectangular emitter plate 48 is joined e.g. welded to the emitter electrode lead 47, and a generally flat rectangular collector plate 50 is joined, e.g., welded to the collector electrode lead 49. The emitter and collector plates may, for example, be about 3.2 mm×4.75 mm. They are arranged parallel to each other. The entire electrode assembly 7 is mounted on the end housing face by engagement of threaded plug 17 into the chamber 15 at the base of housing 3 The flange 52 on base 51 is pressed against the internal annular end face of chamber 15. Preferably, the emitter/collector assembly 7 is positioned on and in the housing 3 so that the emitter and collector plates 48 and 50 are generally parallel to the inlet bore hole 27 and outlet bore hole 33.

Electrode leads 47, 49 become the wires 53 (see FIG. 2) which extend from the emitter and collector electrodes to couplings 70 then to a state-of-the-art voltage source (not shown) and to a state-of-the-art device for measuring the current passing between the emitter and collector electrodes (also not shown). The wires 53 and couplings 70 are held in place by a bracket 55 mounted on housing 3. A temperature sensor 57 well and a heater well are bored into the second end face of housing 3, so that the temperature of the D.I.D. may be controlled and monitored during operation.

Many modifications of the above description are possible without departing from the spirit and scope of the invention. Therefore, the scope of the invention should be determined not from the detailed description of the invention, but from the following claims.

We claim:

1. A discharge ionization detector, comprising:
   a housing having two opposing end faces thereon, said housing having a discharge chamber formed adjacent one end face thereof and an ionization chamber formed adjacent the other end face thereof, the discharge chamber being larger than the ionization chamber; an aperture connecting said chambers;

an electric arc assembly mounted on the end face of said housing adjacent said discharge chamber, the arc electrodes thereof being inside said discharge chamber;

an emitter/collector electrode assembly mounted on the end face of said housing adjacent said ionization chamber, the emitter and collector electrodes thereof being inside said ionization chamber said emitter and collector electrodes comprising an opposing pair of flat parallel electrode faces;

said housing having an inlet in a side wall thereof which communicates with said discharge chamber, a discharge gas being introduced to the discharge chamber through said inlet to be ionized by the action of said electrodes therein so as to form a flow discharge emission which flows through said aperture into said ionization chamber, said flat parallel electrode faces being oriented to direct the glow emission therebetween;

said housing having an inlet in a side wall of said housing which communicates with said ionization chamber and which hereinafter is termed the second inlet, a sample gas being introduced to the ionization chamber through said second inlet becoming admixed with glow discharge gas entering the ionization chamber through said aperture and then passing between said flat parallel electrode faces; and, said housing having an outlet in a side wall thereof which communicates with the ionization chamber, the mixture of glow discharge gas and sample gas passing out of the ionization chamber through said outlet.

2. The detector of claim 1, wherein said housing is cylindrical and each chamber is cylindrical and wherein said flat parallel electrode faces are disposed axially of the cylindrical ionization chamber.

3. The detector of claim 2, wherein said second inlet enters the ionization chamber tangentially.

4. The detector of claim 1, wherein the volume of the discharge chamber is at least five times greater than the volume of the ionization chamber.

5. The detector of claim 1 wherein the volume of the ionization chamber is less than about 500 microliters.

6. The detector of claim 5, wherein the volume of the discharge chamber is at least ten times greater than the volume of the ionization chamber.

7. The detector of claim 1, wherein the discharge chamber is cylindrical and is defined in part by a conical end wall with said aperture at its apex.

8. The detector as claimed in claim 1, wherein the ionization chamber is cylindrical and is defined in part by a conical end wall with said aperture at its apex.

* * * * *